US012751642B2

(12) United States Patent
Liu et al.

(10) Patent No.: US 12,751,642 B2
(45) Date of Patent: Oct. 6, 2026

(54) DEVICE AND METHOD FOR MONITORING THORACIC AND ABDOMINAL BREATHING PATTERNS

(71) Applicant: Guangzhou Medical University, Guangzhou City (CN)

(72) Inventors: Yang Liu, Guangzhou City (CN); Guoxi Xie, Guangzhou City (CN); Shimei Wang, Guangzhou City (CN); Xushi Zhang, Guangzhou City (CN); Keyao Zhang, Guangzhou City (CN)

(73) Assignee: Guangzhou Medical University, Guangzhou City (CN)

( * ) Notice: Subject to any disclaimer, the term of this patent is extended or adjusted under 35 U.S.C. 154(b) by 466 days.

(21) Appl. No.: 18/379,833

(22) Filed: Oct. 13, 2023

(65) Prior Publication Data

US 2024/0335131 A1 Oct. 10, 2024

(30) Foreign Application Priority Data

Apr. 4, 2023 (CN) ......................... 202310348368.6

(51) Int. Cl.
*A61B 5/08* (2006.01)
*A61B 5/00* (2006.01)

(52) U.S. Cl.
CPC .......... *A61B 5/0803* (2013.01); *A61B 5/6805* (2013.01); *A61B 5/6823* (2013.01);
(Continued)

(58) Field of Classification Search
CPC ....... A61B 5/08; A61B 5/0803; A61B 5/0816; A61B 5/1135; A61B 5/6804;
(Continued)

(56) References Cited

U.S. PATENT DOCUMENTS

2011/0060215 A1* 3/2011 Tupin, Jr. ............. A61B 5/6833
600/407
2013/0030257 A1* 1/2013 Nakata ................. A61B 5/0816
600/407

(Continued)

FOREIGN PATENT DOCUMENTS

CN 212261367 U * 1/2021

OTHER PUBLICATIONS

Machine Translation of CN 212261367 U, Clarivate Analytics, 10 pages, printed on Mar. 19, 2026 (Year: 2026).*

*Primary Examiner* — Jennifer Robertson
*Assistant Examiner* — Nidhi N Patel
(74) *Attorney, Agent, or Firm* — CM Law LLP; Robert C. Klinger

(57) ABSTRACT

The present disclosure provides a device and method for monitoring thoracic and abdominal breathing patterns, and relates to the technical field of breathing monitoring. The device includes a wearable vest internally covered with a layer of membrane pressure sensors, a micro control unit (MCU), and a liquid crystal display (LCD). Membrane pressure sensors are disposed in chest, abdomen, and shoulder regions of the wearable vest, and configured to acquire pressure strain values generated by chest, abdomen, and shoulders of a wearer when the wearer is breathing and transmit the pressure strain values to the MCU. The MCU is configured to identify a breathing pattern of the wearer according to the pressure strain values. The LCD is configured to display the pressure strain values of different regions of the wearable vest and the breathing pattern of the wearer in real time three-dimensionally.

10 Claims, 5 Drawing Sheets

(52) U.S. Cl.
CPC ............ *A61B 5/7235* (2013.01); *A61B 5/743* (2013.01); *A61B 2560/02* (2013.01); *A61B 2560/0406* (2013.01); *A61B 2560/045* (2013.01); *A61B 2560/0462* (2013.01); *A61B 2562/0247* (2013.01); *A61B 2562/046* (2013.01)

(58) Field of Classification Search
CPC ... A61B 5/3805; A61B 5/6823; A61B 5/7235; A61B 5/7246; A61B 5/742; A61B 5/743; A61B 2560/02; A61B 2560/0406; A61B 2560/045; A61B 2560/0462; A61B 2560/0247; A61B 2560/0261; A61B 2560/046
See application file for complete search history.

(56) References Cited

U.S. PATENT DOCUMENTS

2019/0274586 A1* 9/2019 Höskuldsson ....... A61B 5/0803
2023/0142080 A1* 5/2023 Cao ...................... A61B 5/6806
600/301

* cited by examiner

DEVICE AND METHOD FOR MONITORING THORACIC AND ABDOMINAL BREATHING PATTERNS

CROSS REFERENCE TO RELATED APPLICATION

This patent application claims the benefit and priority of Chinese Patent Application No. 2023103483686, filed with the China National Intellectual Property Administration on Apr. 4, 2023, the disclosure of which is incorporated by reference herein in its entirety as part of the present application.

TECHNICAL FIELD

The present disclosure relates to the technical field of breathing monitoring, and in particular, to a device and method for monitoring thoracic and abdominal breathing patterns.

BACKGROUND

Breathing, as one of the most important, the most basic vital signs of a human body, contains rich intrinsic physiological information and can reflect the health condition of the human body. Studies have shown that the incidence of breathing system diseases (such as asthma, emphysema, chronic bronchitis, and chronic obstructive pulmonary disease) is increasing year by year. These diseases seriously affect the living quality and living standard of patients who hope urgently that their own diseases can be effectively treated. Common breathing patterns include: abdominal breathing, thoracic breathing, shoulder lifting breathing, inverse breathing, and hybrid breathing. A single breathing pattern or excessive emphasis on one of the breathing patterns may cause problems with the breathing system. Therefore, a normal breathing manner is a balanced combination of breathing patterns. When a breathing manner is adopted excessively or alone, it is usually an abnormal breathing manner.

A doctor needs to know the breathing status of a patient so as to make a decision for next treatment on the one hand; and on the other hand, the doctor needs to make quantitative evaluation on the treatment effect on the patient so as to provide targeted treatment according to the patient's condition. Therefore, an apparatus capable of monitoring breathing signals of the human body in real time continuously and dynamically becomes an essential tool for clinical diagnosis and treatment. However, existing breathing monitoring apparatuses mostly are large in size, complicated in structure, and heavy, and complex in operation, which are utilized only in an ICU ward or a special breathing monitoring ward and are not convenient for moving and home use.

SUMMARY

An objective of the present disclosure is to provide a device and method for monitoring thoracic and abdominal breathing patterns that can comprehensively monitor the pressures of a wearer when the wearer is breathing and provide real-time three-dimensional display, are capable of accurately identifying a breathing pattern of the wearer, and have the characteristic of being portable for wearing.

To achieve the above objective, the present disclosure provides the following technical solutions.

A device for monitoring thoracic and abdominal breathing patterns includes a wearable vest internally covered with a layer of membrane pressure sensors, a micro control unit (MCU), and a liquid crystal display (LCD), where the MCU is connected to the membrane pressure sensors and the LCD separately;

membrane pressure sensors are disposed in chest, abdomen, and shoulder regions of the wearable vest, and configured to acquire pressure strain values generated by chest, abdomen, and shoulders of a wearer when the wearer is breathing and transmit the pressure strain values to the MCU; the MCU is configured to identify a breathing pattern of the wearer according to the pressure strain values; and the LCD is configured to display the pressure strain values of different regions of the wearable vest and the breathing pattern of the wearer in real time three-dimensionally.

Alternatively, the device for monitoring thoracic and abdominal breathing patterns may further include a data selector, where the data selector is connected to membrane pressure sensors and the MCU separately; and the MCU is configured to select, by means of the data selector, a current membrane pressure sensor that acquires the pressure strain value.

Alternatively, the device for monitoring thoracic and abdominal breathing patterns may further include a touch screen, where the touch screen is connected to the MCU and the LCD separately; and a display angle of the wearable vest is changed by sliding on the touch screen.

Alternatively, the MCU may be a STM32 series chip.

A method for monitoring thoracic and abdominal breathing patterns, which is based on the device for monitoring thoracic and abdominal breathing patterns, includes:

- receiving, by an MCU, pressure strain values generated by chest, abdomen, and shoulders of a wearer when the wearer is breathing and acquired by membrane pressure sensors;
- calculating a thoracic breathing contribution ratio, an abdominal breathing contribution ratio, and a shoulder movement amplitude based on the pressure strain values; and
- identifying a breathing pattern of the wearer based on the thoracic breathing contribution ratio, the abdominal breathing contribution ratio, and the shoulder movement amplitude.

Alternatively, the receiving, by an MCU, pressure strain values generated by chest, abdomen, and shoulders of a wearer when the wearer is breathing and acquired by membrane pressure sensors may specifically include:

- selecting, by the MCU by means of a data selector, a current membrane pressure sensor that acquires the pressure strain value, and receiving the pressure strain value acquired by the current membrane pressure sensor at intervals of 1 ms by means of a systick_handler function.

Alternatively, the calculating a thoracic breathing contribution ratio, an abdominal breathing contribution ratio, and a shoulder movement amplitude based on the pressure strain values may specifically include:

- calculating the thoracic breathing contribution ratio $CR_{chest}$ by a formula $$CR_{chest} = \frac{\overline{P}_{chest}}{\overline{P}_{chest} + \overline{P}_{abdomen}},$$

where $\overline{P}_{chest}$ represents an average value of all pressure strain values of a chest region of a wearable vest; and $\overline{P}_{abdomen}$ represents an average value of all pressure strain values of an abdomen region of the wearable vest;

calculating the abdominal breathing contribution ratio $CR_{abdomen}$ by a formula $$CR_{abdomen} = \frac{\overline{P}_{abdomen}}{\overline{P}_{chest} + \overline{P}_{abdomen}};$$

and calculating an average value of all pressure strain values of a shoulder region of the wearable vest as the shoulder movement amplitude.

Alternatively, the identifying a breathing pattern of the wearer based on the thoracic breathing contribution ratio, the abdominal breathing contribution ratio, and the shoulder movement amplitude may specifically include:

when $20\% \leq CR_{chest} \leq 40\%$ and $60\% \leq CR_{abdomen} \leq 80\%$ identifying that the breathing pattern of the wearer is normal breathing;

when $CR_{chest} >> 40\%$, identifying that the breathing pattern of the wearer is excessive thoracic breathing;

when $CR_{abdomen} >> CR_{chest}$ identifying that the breathing pattern of the wearer is excessive abdominal breathing; and when the shoulder movement amplitude is greater than a shoulder movement amplitude threshold, identifying that the breathing pattern of the wearer is excessive shoulder lifting breathing.

Alternatively, the method for monitoring thoracic and abdominal breathing patterns may further include:

converting the pressure strain values of the chest and the abdomen into breathing amplitudes; and plotting thoracic and abdominal breathing movement curves based on the breathing amplitudes, and displaying the thoracic and abdominal breathing movement curves on an LCD.

Alternatively, the method for monitoring thoracic and abdominal breathing patterns may further include: marking a position of each membrane pressure sensor by dotting on the LCD, and representing a magnitude of a pressure strain value acquired by the corresponding membrane pressure sensor by a color shade of a dot.

According to specific embodiments provided in the present disclosure, the present disclosure has the following technical effects:

The present disclosure provides a device and method for monitoring thoracic and abdominal breathing patterns. The pressures of a wearer when the wearer is breathing can be comprehensively monitored and the breathing patterns thereof can be accurately identified by separately connecting the MCU to the LCD and a layer of membrane pressure sensors internally provided in the wearable vest, where membrane pressure sensors are disposed in the chest, abdomen, and shoulder regions of the wearable vest. The pressure strain values of different regions of the wearable vest and the breathing pattern of the wearer are displayed by the LCD in real time three-dimensionally. Moreover, the device for monitoring thoracic and abdominal breathing patterns has the characteristic of being portable for wearing.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

DETAILED DESCRIPTION OF THE EMBODIMENTS

The technical solutions in the embodiments of the present disclosure will be clearly and completely described below with reference to the accompanying drawings in the embodiments of the present disclosure. Apparently, the described embodiments are merely a part rather than all the embodiments of the present disclosure. All other embodiments derived from the embodiments in the present disclosure by a person of ordinary skill in the art without creative efforts shall fall within the protection scope of the present disclosure.

With the development of the embedded and mobile technologies, wearables have gradually entered the market. Wearables can not only satisfy portable use, but also sense and record different objects (including the myodynamia, blood oxygen, and the like of a user) in ingenious combination with sensors, thus realizing multiple functions.

An objective of the present disclosure is to provide a device and method for monitoring thoracic and abdominal breathing patterns that can comprehensively monitor the pressures of a wearer when the wearer is breathing and provide real-time three-dimensional display, are capable of accurately identifying a breathing pattern of the wearer, and have the characteristic of being portable for wearing.

In order to make the above objective, features, and advantages of the present disclosure clearer and more comprehensible, the present disclosure will be further described in detail below in combination with the accompanying drawings and the specific embodiments.

Figure 1:
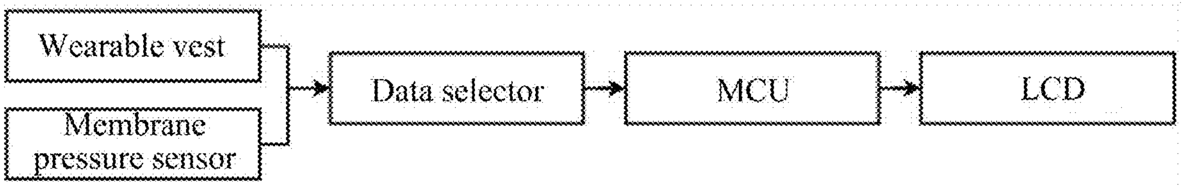
FIG. 1 is a schematic diagram illustrating a connection structure of a device for monitoring thoracic and abdominal breathing patterns provided by the present disclosure.

FIG. 1 is a schematic diagram illustrating a connection structure of a device for monitoring thoracic and abdominal breathing patterns in the present disclosure, and FIG. 2 to FIG. 6 are schematic diagrams illustrating an outline of a device for monitoring thoracic and abdominal breathing patterns in the present disclosure, and positions of sampling points of membrane pressure sensors disposed on a front, a back, and a side thereof, and when viewed from the top, respectively. As shown in FIG. 1, the present disclosure provides a device for monitoring thoracic and abdominal breathing patterns is composed of a wearable vest internally covered with a layer of membrane pressure sensors, a micro control unit (MCU), and a liquid crystal display (LCD), where the MCU is connected to the membrane pressure sensors and the LCD separately.

Membrane pressure sensors are disposed in chest, abdomen, and shoulder regions of the wearable vest, and configured to acquire pressure strain values generated by chest, abdomen, and shoulders of a wearer when the wearer is breathing and transmit the pressure strain values to the MCU. The MCU is configured to identify a breathing pattern of the wearer according to the pressure strain values.

Specifically, the MCU uses STM32 series chip as a main control core, and is configured to acquire pressure strain value signals of the membrane pressure sensors at the left and right shoulders, chest, and abdomen of the wearer, analyze variations of the pressure strain value from sampling points in each region to identify the breathing pattern of the wearer, and finally determine whether the breathing pattern of the wearer is normal.

Specifically, membrane pressure sensors are embedded in the inner layer of the wearable vest using the embedded integration technology, and body-fitting streamlined spaced sampling points are provided along the shoulders, neck, chest, and abdomen of the wearer to form a pressure membrane. The membrane pressure sensors closely fitting the body are utilized to accurately capture pressure strain value variations caused by the chest and abdomen lifting up and down when the wearer is breathing. The sampling points of the sensors at the left and right shoulders are mainly configured to acquire the pressure strain values of the shoulders when the wearer is breathing so as to identify shoulder lifting breathing. The sampling points of the sensors surrounding the chest and the abdomen are mainly configured to acquire the pressure strain values of the chest and the abdomen when the wearer is breathing so as to comprehensively identify thoracic breathing, abdominal breathing, hybrid breathing, and inverse breathing.

The LCD is configured to display the pressure strain values of different regions of the wearable vest and the breathing pattern of the wearer in real time three-dimensionally. Specifically, as shown in FIG. 2 to FIG. 6, the STM32 series chip is connected to the LCD so that the pressure strain value sampling points of the wearable vest at different angles can be displayed.

Referring to FIG. 1, In a preferred embodiment, the device for monitoring thoracic and abdominal breathing patterns is further provided with a data selector. The data selector is connected to membrane pressure sensors and the MCU separately, where the MCU is configured to select, by means of the data selector, a current membrane pressure sensor that acquires the pressure strain value.

Specifically, because of a large number of membrane pressure sensors, the MCU is further provided with analog-to-digital conversion (ADC) acquisition units for use in combination with the data selector, allowing for selection of the current membrane pressure sensor that acquires the pressure strain value by means of the data selector in a progressive scanning manner.

In a preferred embodiment, the device for monitoring thoracic and abdominal breathing patterns is further provided with a touch screen. The touch screen is connected to the MCU and the LCD respectively, and a display angle of the wearable vest can be switched by sliding on the touch screen. Therefore, chest and abdomen sampling phase difference points at different angles can be displayed omni-directionally by sliding on the touch screen.

The present disclosure further provides a method for monitoring thoracic and abdominal breathing patterns. Firstly, an MCU receives pressure strain values generated by chest, abdomen, and shoulders of a wearer when the wearer is breathing and acquired by membrane pressure sensors.

In a preferred embodiment, the MCU selects a current membrane pressure sensor that acquires the pressure strain value by means of a data selector, and the pressure strain value acquired by the current membrane pressure sensor is received at intervals of 1 ms by means of a systick_handler function.

Specifically, an ADC acquisition program code is run in the systick_handler function of the STM32 series chip. The systick_handler function is an interrupt function with 1 ms as a time reference. That is, the systick_handler function is run at intervals of 1 ms to achieve the purpose of rapidly acquiring output pressure values from the pressure membrane of the device in different regions.

Moreover, to improve the acquisition efficiency, acquisition points are provided in the present disclosure and simultaneous scanning by units is realized. Thus, ADC single-channel acquisition cannot meet the requirement. Therefore, a multi-ADC channel polling cyclic acquisition mode is adopted in the present disclosure to achieve the desired purpose.

A thoracic breathing contribution ratio, an abdominal breathing contribution ratio, and a shoulder movement amplitude are calculated based on the pressure strain values.

In a preferred embodiment, the thoracic breathing contribution ratio $CR_{chest}$ is calculated by a formula $$CR_{chest} = \frac{\overline{P}_{chest}}{\overline{P}_{chest} + \overline{P}_{abdomen}},$$

where $\overline{P}_{chest}$ represents an average value of all pressure strain values of a chest region of a wearable vest; and $\overline{P}_{abdomen}$ represents an average value of all pressure strain values of an abdomen region of the wearable vest. The abdominal breathing contribution ratio $CR_{abdomen}$ is calculated by a formula $$CR_{abdomen} = \frac{\overline{P}_{abdomen}}{\overline{P}_{chest} + \overline{P}_{abdomen}}.$$

An average value of all pressure strain values of a shoulder region of the wearable vest is calculated as the shoulder movement amplitude.

Specifically, in the present disclosure, the pressure membrane operates to monitor the pressure values generated on the surface of the device due the relative movements between the chest, abdomen, and shoulders of the wearer, and the device when the wearer is breathing. Firstly, the pressure membrane is divided into regions, specifically into chest, abdomen, and shoulder regions. The pressure value of each region is obtained by calculating an average value of the pressure strain values acquired by all the membrane pressure sensors in the region. The pressure value of the shoulder region is obtained through pressure detection. That is, a shoulder breathing amplitude is obtained and saved.

Figure 7:
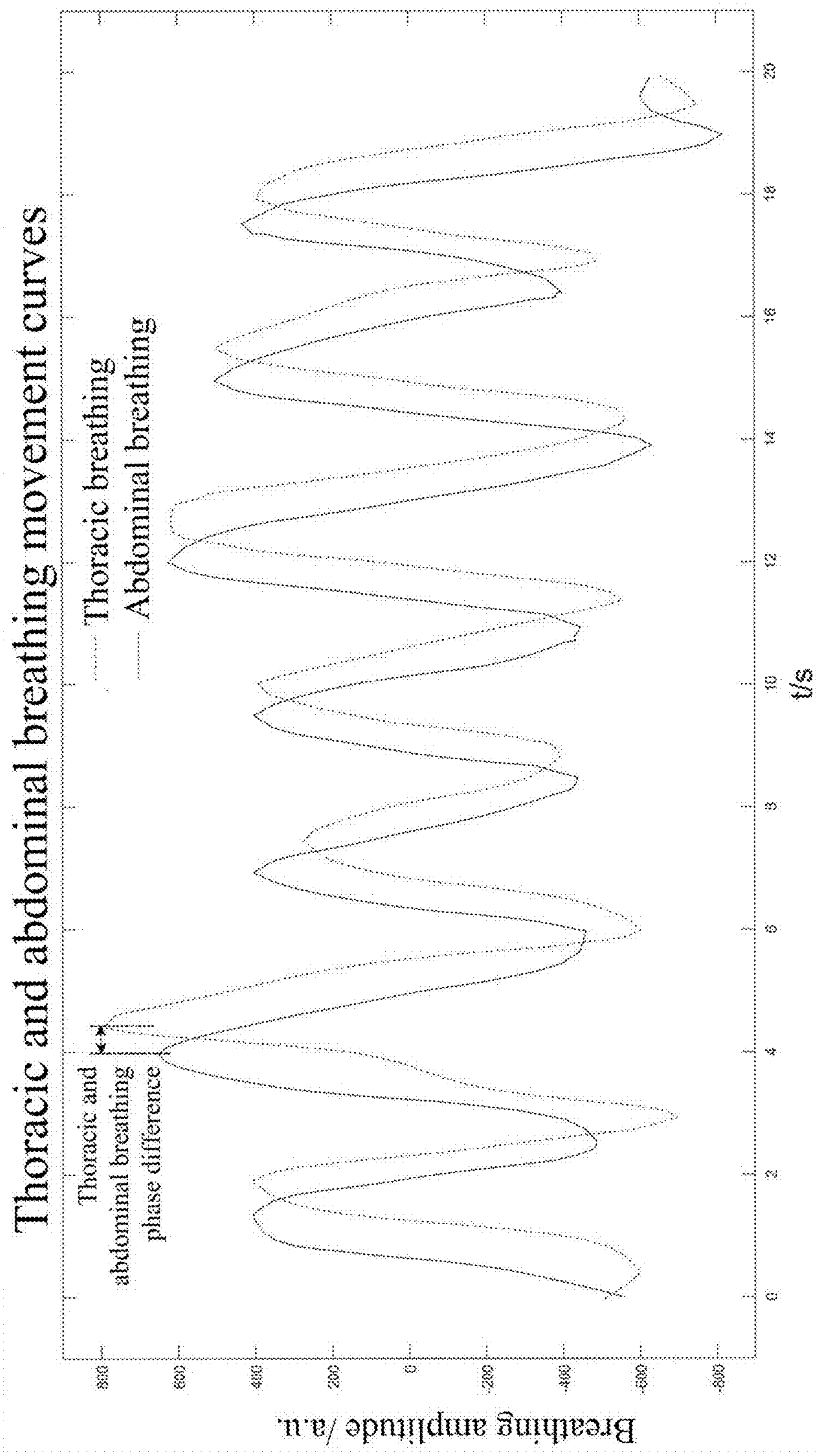
FIG. 7 is a schematic diagram illustrating thoracic and abdominal breathing movement curves of a wearer.

FIG. 7 is a schematic diagram illustrating thoracic and abdominal breathing movement curves of a wearer, where the horizontal axis represents t and the vertical axis thereof represents a breathing amplitude. As shown in FIG. 7, the pressure values of the chest and abdomen regions are obtained through pressure detection. That is, the breathing amplitudes of the chest and abdomen of the wearer are obtained, and then thoracic and abdominal breathing movement curves are obtained. The curves are visually displayed on an LCD, assisting a doctor with observing the breathing status of a patient.

Meanwhile, a certain number of breathing pressure data values of the chest, the abdomen, the shoulders are saved in real time in the STM32 series single chip with an array of a certain length as a container, and calculated to obtain the following parameters:

- the thoracic breathing contribution ratio, which is a ratio of the average value of the pressure strain values of the chest region to the sum of the average values of the pressure strain values of the chest and the abdomen;
- the abdominal breathing contribution ratio, which is a ratio of the average value of the pressure strain values of the abdomen region to the sum of the average values of the pressure strain values of the chest and the abdomen; and
- the shoulder movement amplitude, which is obtained from the average value of the pressure strain values acquired by all the membrane pressure sensors in the shoulder region.

Identifying a breathing pattern of the wearer based on the thoracic breathing contribution ratio, the abdominal breathing contribution ratio, and the shoulder movement amplitude specifically includes:

- when $20\% \leq CR_{chest} \leq 40\%$ and $60\% \leq CR_{abdomen} \leq 80\%$, identify that the breathing pattern of the wearer is normal breathing;
- when $CR_{chest} >> 40\%$, identify that the breathing pattern of the wearer is excessive thoracic breathing;
- when $CR_{abdomen} >> CR_{chest}$ identify that the breathing pattern of the wearer is excessive abdominal breathing; and
- when the shoulder movement amplitude is greater than a shoulder movement amplitude threshold, identify that the breathing pattern of the wearer is excessive shoulder lifting breathing.

Specifically, the contributions of different regions of the wearer to breathing and thoracic and abdominal breathing coordination are quantitatively known so as to identify the current breathing pattern. When the thoracic breathing contribution ratio is within a range of 20% to 40% and the abdominal breathing contribution ratio is within a range of 60% to 80%, normal breathing is identified. When the thoracic breathing contribution ratio is far beyond the range of 20% to 40%, excessive thoracic breathing is identified. When the abdominal breathing contribution ratio is far greater than the thoracic breathing contribution ratio, excessive abdominal breathing is identified. When the shoulder movement amplitude is greater than a threshold, excessive shoulder lifting breathing is identified, where the threshold is usually an amplitude value of the shoulders of the human body lifting up by 1 cm detected by the membrane pressure sensors.

As shown in FIG. 7, the pressure strain values of the chest and the abdomen may be transformed into breathing amplitudes; and then thoracic and abdominal breathing movement curves are plotted based on the breathing amplitudes, and displayed on the LCD.

Specifically, after receiving the pressure values input by the pressure membrane through ADC channels, the MCU calculates the average value of the pressure strain values acquired by all the membrane pressure sensors in a region as the pressure value of the region, and can indirectly transform the pressure values of the obtained chest and the abdomen into breathing curves synchronously and display the breathing curves at the bottom of the LCD. Meanwhile, the thoracic breathing contribution ratio and the abdominal breathing contribution ratio are calculated from the ratios of the average values of the pressure strain values of the chest and the abdomen to the average value of the pressure strain values of the chest region. Thus, the contributions of different parts of the wearer to breathing can be quantitatively known so as to identify the breathing pattern of the current user.

In a preferred embodiment, in the present disclosure, a position of each membrane pressure sensor is marked by dotting on the LCD, and a magnitude of a pressure strain value acquired by the corresponding membrane pressure sensor is represented by a color shade of a dot.

Figure 2:
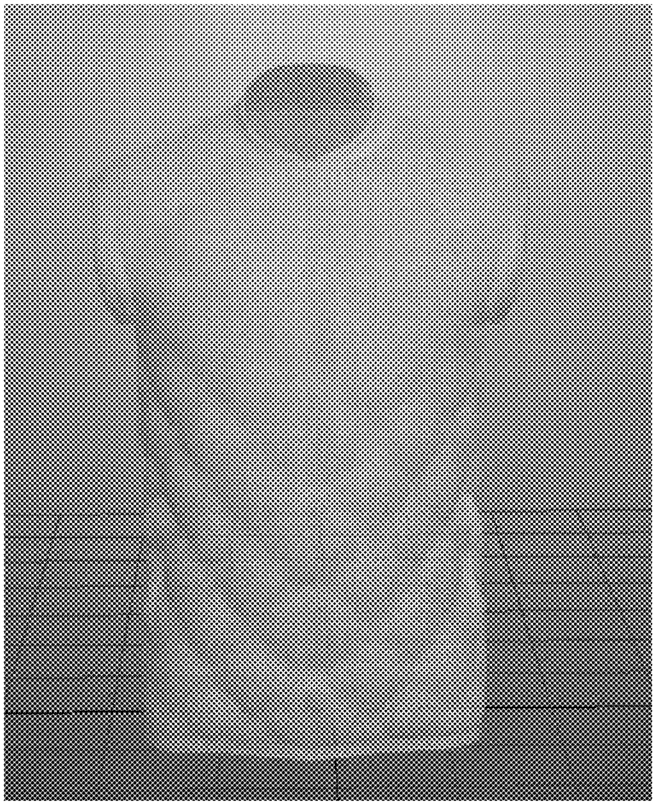
FIG. 2 is a schematic diagram illustrating an outline of a device for monitoring thoracic and abdominal breathing patterns provided by the present disclosure.
Figure 3:
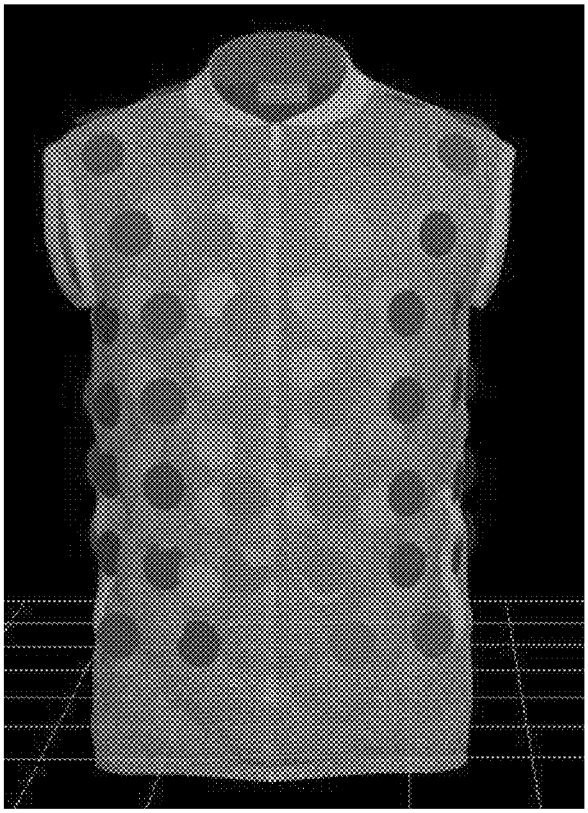
FIG. 3 is a schematic diagram illustrating positions of sampling points on a front of a device for monitoring thoracic and abdominal breathing patterns provided by the present disclosure.
Figure 4:
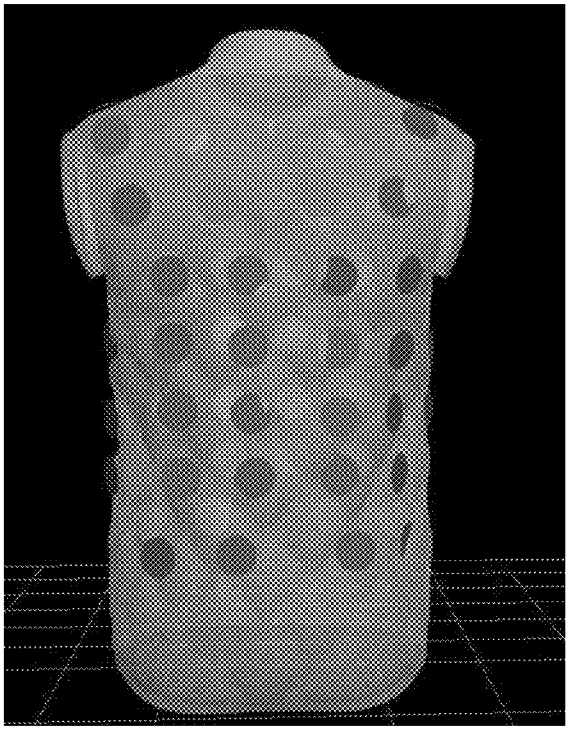
FIG. 4 is a schematic diagram illustrating positions of sampling points on a back of a device for monitoring thoracic and abdominal breathing patterns provided by the present disclosure.
Figure 5:
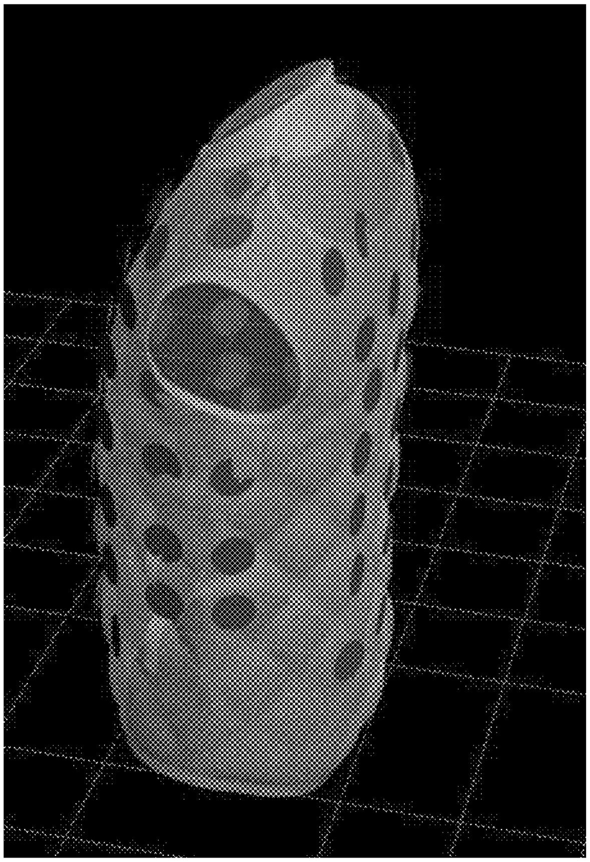
FIG. 5 is a schematic diagram illustrating positions of sampling points on a side of a device for monitoring thoracic and abdominal breathing patterns provided by the present disclosure.
Figure 6:
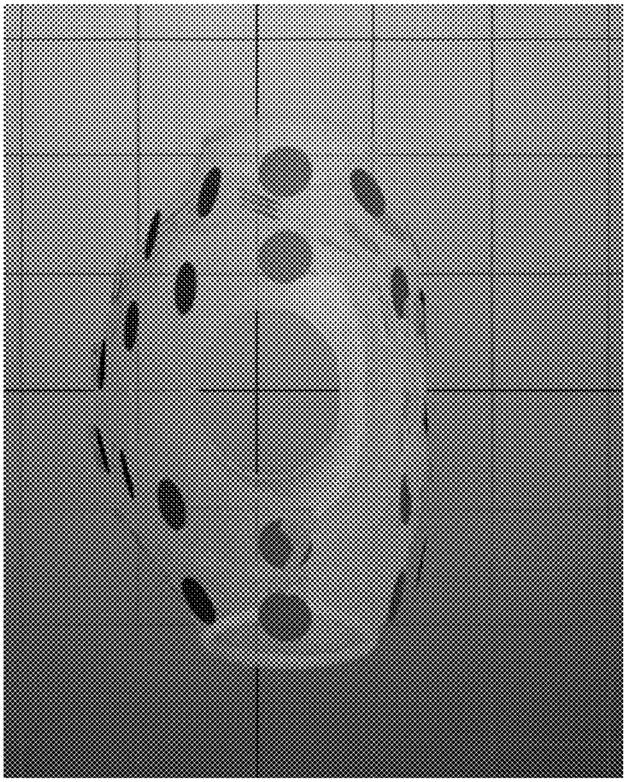
FIG. 6 is a schematic diagram illustrating sampling points of a device for monitoring thoracic and abdominal breathing patterns provided by the present disclosure viewed from the top.

Specifically, to three-dimensionally display the pressure values of different regions of the human body when the wearer is breathing more visually and accurately in the present disclosure, a three-dimensional diagram of the wearable vest is displayed on the LCD, as shown in FIG. 2. Meanwhile, the position of each membrane pressure sensor is marked by dotting in the diagram, and the magnitude of the pressure strain value acquired by the corresponding membrane pressure sensor is represented by the color shade of the dot. Moreover, a display and interaction touch screen for the three-dimensional wearable vest is provided based on the LCD, and the display angel can be switched by sliding on the touch screen so as to omni-directionally display dark and light colors of the pressure points of the wearable vest in all directions.

Furthermore, in the present disclosure, a static flag variable is set in a built-in program of the MCU to record the breathing patterns of the current user. Specifically, when the static flag variable is 1, it indicates normal breathing. When the static flag variable is 2, it indicates excessive thoracic breathing. When the static flag variable is 3, it indicates excessive abdominal breathing. When the static flag variable is 4, it indicates shoulder lifting breathing; and meanwhile, the static flag variable is initialized to 0.

The MCU transfers the static flag variable to the LCD and controls the display of the breathing patterns on the LCD with the values of the static flag variable.

The LCD receives a control signal from the MCU. When a received value is 1, a character string displayed at the bottom of the LCD is "normal breathing". When the received value is 2, the character string displayed at the bottom of the LCD is "excessive thoracic breathing". When the received value is 3, the character string displayed at the bottom of the LCD is "excessive abdominal breathing". When the received value is 4, the character string displayed at the bottom of the LCD is "excessive shoulder lifting breathing". In subsequent development, a correspondence of the static flag variable to a breathing pattern may be changed correspondingly.

In the present disclosure, the pressure membrane is embedded into the customized wearable vest using the embedded integration technology, and the pressures of the wearer when the wearer is breathing are monitored through three-dimensional pressure detection and displayed three-dimensionally in real time, thus further assisting in identifying the breathing pattern of the wearer.

Compared with existing breathing monitoring instruments on the market, the device for monitoring thoracic and abdominal breathing patterns provided in the present disclosure has the following advantages.

1. The device for monitoring thoracic and abdominal breathing patterns in the present disclosure is wearable for a long time and has the characteristic of being portable for wearing. Moreover, the device of the present disclosure is more convenient than a wearable oral breathing monitor and a nasal breathing monitoring device, and can be used in scenarios such as home, office, and outside, realizing continuous monitoring.
2. The device for monitoring thoracic and abdominal breathing patterns in the present disclosure monitors the pressures of the wearer when the wearer is breathing through three-dimensional pressure detection and provides real-time three-dimensional display, and can visually display the omni-directional stress condition of the wearable vest on the LCD, assisting the wearer or a doctor to know the current breathing pattern of the wearer in real time.
3. The device for monitoring thoracic and abdominal breathing patterns in the present disclosure realizes accurate identification of breathing patterns. The wearable vest acquires, by means of the built-in pressure membrane, pressure strain values and transmits the data to the MCU so that the current breathing pattern of the wearer can be analyzed rapidly and accurately and displayed in real time. The device of the present disclosure has the characteristics of good identification effect, rapid identification, and simple implementation process.
4. The device for monitoring thoracic and abdominal breathing patterns in the present disclosure realizes comprehensive monitoring on the breathing patterns of the wearer. Existing chest and abdomen pressure measuring devices on the market typically use a limited number of pressure detection points to detect pressures, and thus have certain limitations. The device of the present disclosure may accurately identify breathing patterns by monitoring the pressure strain values of different points of the shoulders, neck, chest, and abdomen of the wearer in real time using the built-in pressure membrane of the wearable vest.

In conclusion, compared with the prior art, the present disclosure may realize real-time three-dimensional pressure detection of the human body and display the detected pressure values on the LCD in real time in the form of a three-dimensional image, and can accurately monitor the surface pressure of the human body when the wearer is breathing. Moreover, in the present disclosure, the pressure values of the human body when the wearer is breathing may be acquired for determining the dilatation movements of the chest, abdomen, and shoulders of the human body when the wearer is breathing, thus determining the breathing patterns and assisting a doctor with knowing the physical condition of the user when the wearer is breathing. The device is also portable for wearing, applicable to scenarios, and capable of performing long-time continuous breathing monitoring.

Therefore, the present disclosure overcomes the shortcomings of complicated implementation, complex operation, large size, using experience, and the like of the existing breathing monitoring apparatus on the market, and has the characteristics of portability, rapid and accurate identification, and visual display.

The embodiments are described herein in a progressive manner. Each embodiment focuses on the difference from another embodiment, and the same and similar parts between the embodiments may refer to each other.

Specific examples are used herein for illustration of the principles and embodiments of the present disclosure. The description of the foregoing embodiments is used to help illustrate the method of the present disclosure and the core principles thereof. In addition, those of ordinary skill in the art can make various modifications in terms of specific embodiments and scope of application in accordance with the teachings of the present disclosure. In conclusion, the content of the description shall not be construed as limitations to the present disclosure.

What is claimed is:

1. A device for monitoring thoracic and abdominal breathing patterns, comprising a wearable vest internally covered with a layer of membrane pressure sensors, a micro control unit (MCU), and a liquid crystal display (LCD), wherein the MCU is connected to the membrane pressure sensors and the LCD separately;

the membrane pressure sensors are disposed in chest, abdomen, and shoulder regions of the wearable vest, and configured to acquire pressure strain values generated by chest, abdomen, and shoulders of a wearer when the wearer is breathing and transmit the pressure strain values to the MCU; the MCU is configured to identify a breathing pattern of the wearer according to the pressure strain values; and the LCD is configured to display the pressure strain values generated by the chest, the abdomen, and the shoulders of the wearer and the breathing pattern of the wearer in real time three-dimensionally;

the MCU is configured to: receive the pressure strain values generated by the chest, the abdomen, and the shoulders of the wearer when the wearer is breathing and acquired by the membrane pressure sensors; calculate a thoracic breathing contribution ratio, an abdominal breathing contribution ratio, and a shoulder movement amplitude based on the pressure strain values; and identify the breathing pattern of the wearer based on the thoracic breathing contribution ratio, the abdominal breathing contribution ratio, and the shoulder movement amplitude.

2. The device for monitoring thoracic and abdominal breathing patterns according to claim 1, further comprising a data selector, wherein the data selector is connected to the membrane pressure sensors and the MCU separately; and the MCU is configured to select, by means of the data selector, a current membrane pressure sensor from the membrane pressure sensors that acquires a corresponding pressure strain value of the pressure strain values.

3. The device for monitoring thoracic and abdominal breathing patterns according to claim 1, further comprising a touch screen, wherein the touch screen is connected to the MCU and the LCD separately, and configured to change a display angle of the wearable vest by sliding on the touch screen.

4. The device for monitoring thoracic and abdominal breathing patterns according to claim 1, wherein the MCU is a STM32 series chip.

5. A method for monitoring thoracic and abdominal breathing patterns, based on a device for monitoring thoracic and abdominal breathing patterns comprising a wearable vest internally covered with a layer of membrane pressure sensors, a micro control unit (MCU), and a liquid crystal display (LCD), wherein the MCU is connected to the membrane pressure sensors and the LCD separately; the membrane pressure sensors are disposed in chest, abdomen, and shoulder regions of the wearable vest, and configured to acquire pressure strain values generated by chest, abdomen, and shoulders of a wearer when the wearer is breathing and transmit the pressure strain values to the MCU; the MCU is configured to identify a breathing pattern of the wearer according to the pressure strain values; and the LCD is configured to display the pressure strain values generated by the chest, the abdomen, and the shoulders of the wearer and the breathing pattern of the wearer in real time three-dimensionally;

the method comprising:

receiving, by the MCU, the pressure strain values generated by the chest, the abdomen, and the shoulders of the wearer when the wearer is breathing and acquired by the membrane pressure sensors;

calculating a thoracic breathing contribution ratio, an abdominal breathing contribution ratio, and a shoulder movement amplitude based on the pressure strain values; and identifying the breathing pattern of the wearer based on the thoracic breathing contribution ratio, the abdominal breathing contribution ratio, and the shoulder movement amplitude.

6. The method for monitoring thoracic and abdominal breathing patterns according to claim 5, wherein the receiving, by the MCU, the pressure strain values generated by the chest, the abdomen, and the shoulders of the wearer when the wearer is breathing and acquired by the membrane pressure sensors specifically comprises:

selecting, by the MCU by means of a data selector, a current membrane pressure sensor from the membrane pressure sensors that acquires a corresponding pressure strain value of the pressure strain values, and receiving the corresponding pressure strain value acquired by the current membrane pressure sensor at intervals of 1 ms by means of a systick_handler function.

7. The method for monitoring thoracic and abdominal breathing patterns according to claim 5, wherein the calculating the thoracic breathing contribution ratio, the abdominal breathing contribution ratio, and the shoulder movement amplitude based on the pressure strain values specifically comprises:

calculating the thoracic breathing contribution ratio $CR_{chest}$ by a formula $$CR_{chest} = \frac{\overline{P}_{chest}}{\overline{P}_{chest} + \overline{P}_{abdomen}},$$

wherein $\overline{P}_{chest}$ represents an average value of all pressure strain values of the chest region of the wearable vest; and $\overline{P}_{abdomen}$ represents an average value of all pressure strain values of the abdomen region of the wearable vest;

calculating the abdominal breathing contribution ratio $CR_{abdomen}$ by a formula $$CR_{abdomen} = \frac{\overline{P}_{abdomen}}{\overline{P}_{chest} + \overline{P}_{abdomen}};$$

and calculating an average value of all pressure strain values of the shoulder region of the wearable vest as the shoulder movement amplitude.

8. The method for monitoring thoracic and abdominal breathing patterns according to claim 7, wherein the identifying the breathing pattern of the wearer based on the thoracic breathing contribution ratio, the abdominal breathing contribution ratio, and the shoulder movement amplitude specifically comprises:

when $20\% \leq CR_{chest} \leq 40\%$ and $60\% \leq CR_{abdomen} \leq 80\%$, identifying that the breathing pattern of the wearer is normal breathing;

when $CR_{chest} >> 40\%$, identifying that the breathing pattern of the wearer is excessive thoracic breathing;

when $CR_{abdomen} >> CR_{chest}$, identifying that the breathing pattern of the wearer is excessive abdominal breathing; and when the shoulder movement amplitude is greater than a shoulder movement amplitude threshold, identifying that the breathing pattern of the wearer is excessive shoulder lifting breathing.

9. The method for monitoring thoracic and abdominal breathing patterns according to claim 7, further comprising:

converting the pressure strain values of the chest and the abdomen into breathing amplitudes; and plotting thoracic and abdominal breathing movement curves based on the breathing amplitudes, and displaying the thoracic and abdominal breathing movement curves on the LCD.

10. The method for monitoring thoracic and abdominal breathing patterns according to claim 5, further comprising: marking a position of each membrane pressure sensor by dotting on the LCD, and representing a magnitude of a pressure strain value of the pressure strain values acquired by a corresponding membrane pressure sensor of the membrane pressure sensors by a color shade of a dot.

* * * * *